United States Patent [19]

Kim

[11] Patent Number: 5,480,402
[45] Date of Patent: Jan. 2, 1996

[54] SHOULDER COMPRESSION INTERLOCKING SYSTEM

[76] Inventor: Andrew C. Kim, 30213 Del Rey Rd., Temecula, Calif. 92591

[21] Appl. No.: 102,473

[22] Filed: Aug. 5, 1993

[51] Int. Cl.⁶ ............................................. A61B 17/72
[52] U.S. Cl. ........................................ 606/64; 606/98
[58] Field of Search .................... 606/62, 64, 65, 606/66, 67, 72, 96, 98, 104, 87, 89; 128/898

[56] References Cited

U.S. PATENT DOCUMENTS

| | | | |
|---|---|---|---|
| 4,622,959 | 11/1986 | Marcus | 606/64 |
| 4,911,153 | 3/1990 | Border | 606/98 |
| 5,281,224 | 1/1994 | Faccioli et al. | 606/62 |

FOREIGN PATENT DOCUMENTS 384359  11/1987  Austria.

Primary Examiner—Tamara L. Graysay
Attorney, Agent, or Firm—Baker, Maxham, Jester & Meador

[57] ABSTRACT

A compression interlocking system for stabilizing shoulder fractures comprises an elongated intramedullary rod for extending within a bore generally parallel to the longitudinal axis of the humerus from the proximal end of the humerus to beyond the fracture, a pair of proximal transverse bores in the rod for positioning proximate the fracture, and a pair of proximal lag screws for extending across said fracture and through said transverse bores.

16 Claims, 2 Drawing Sheets

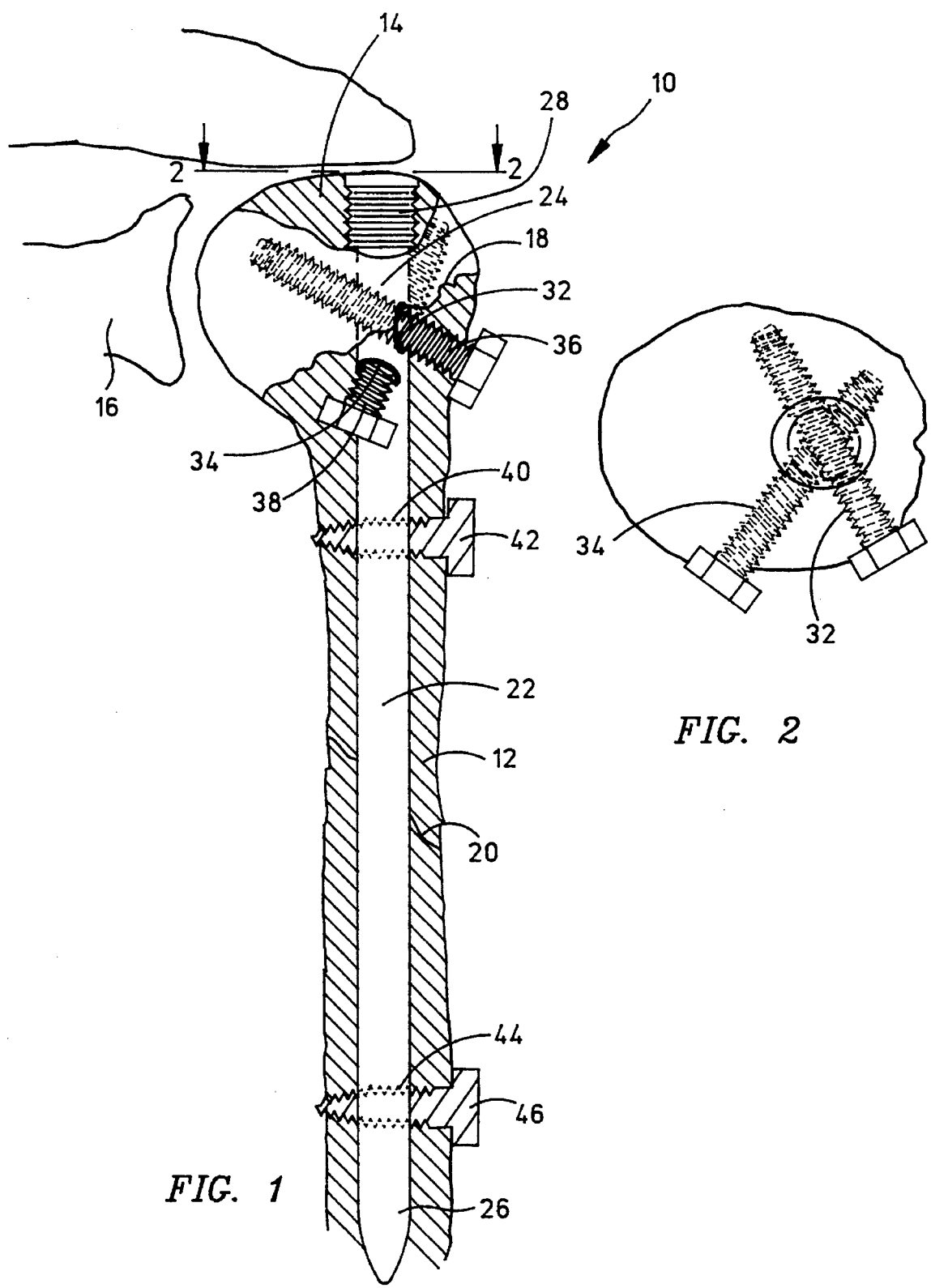

SHOULDER COMPRESSION INTERLOCKING SYSTEM

BACKGROUND OF THE INVENTION

The present invention relates to medical devices and pertains particularly to an improved orthopedic device for the repair of shoulder fractures.

Fractures of the arm and shoulders, particularly in the elderly population, are a quite common occurrence. More particularly, fractures in the proximal region of the humerus is very common. Early mobilization of the shoulder and arm following injury is important to early healing and rehabilitation of such injuries.

The present methods and apparatus for fixation of fractures do not provide a satisfactory internal fixation to enable early mobilization. The bony substance of the proximal fragment is frequently insufficient for good purchase of fixation using current apparatus and methods.

The presently known internal fixation devices for such a fracture do not give a suitable stable construct. For example, open reduction internal fixation with the RUSH-rod or other intramedullary system does not give a suitable rigid system to allow the patient to have early mobilization. All of these known systems frequently require disruption of the supraspinatus tendon and articular surface, because the extra articular bony substance is very limited in this type of fracture. The deforming forces of the various tendons frequently cause a proximal fragment to be rotated. It is very difficult to reduce and maintain the reduction in rotation with conventional existing methods of internal fixation, because they do not give any compressive effect. Similarly, because of the limited space in the subacromial region and the deforming tension force by the tendon, reduction and internal fixation is frequently impossible.

Other known methods, such as closed reduction and percutaneous STEINMEN fixation, do not provide a stable fixation. This is especially a problem in osteoporotic bones where the fixation easily fails and the reduction is frequently lost.

Accordingly, it is desirable that an improved stable construct with compression and interlocking fixation that will maintain the reduction and permit early, more aggressive mobilization to enable faster recovery be available.

SUMMARY AND OBJECTS OF THE INVENTION

It is the primary object of the present invention to provide an improved orthopedic apparatus for the repair of shoulder fractures.

In accordance with a primary aspect of the present invention a compression interlocking system for stabilizing shoulder fractures, comprises elongated intramedullary rod means for extending within a bore generally parallel to the longitudinal axis of the humerus from the proximal end of the humerus to beyond the fracture, a pair of proximal transverse bores in the pin means for positioning proximate the fracture, and a pair of proximal lag screws for extending across said fracture and through said transverse bores.

BRIEF DESCRIPTION OF THE DRAWING

The above and other objects and advantages of the present invention will become apparent from the following description when read in conjunction with the accompanying drawings wherein:

FIG. 1 is a front elevation view partially in section of a preferred embodiment of the invention shown in use;

FIG. 2 is a view taken generally on line 2—2 of FIG. 1;

DETAILED DESCRIPTION OF A PREFERRED EMBODIMENT

Figure 5:
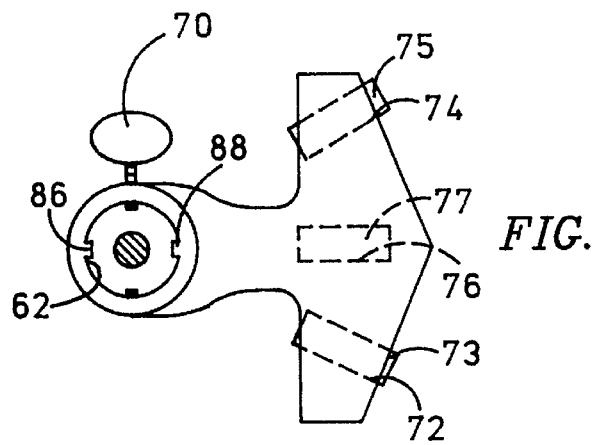
FIG. 5 is a top view of the guide assembly of FIG. 3 with the hand screw removed.

Referring now to the drawing, and particularly to FIG. 1, there is illustrated a partial view of a shoulder area of a human skeleton, designated generally by the numeral 10 illustrating an apparatus in accordance with the invention in position for the repair of multiple fractures. The skeleton of the upper arm consists of a single bone, the humerus. The humerus is the longest and largest bone of the arm. The humerus comprises a shaft 12 having a generally cylindrical configuration, with an upper or proximal end as illustrated and a lower or distal end, not shown. The upper end is formed of a large rounded head 14 joined to the shaft by a constricted neck portion. The head 14 is nearly hemispherical in form, and is directed upward, inward and a little backward. It articulates with the glenoid cavity of the scapula 16.

The illustrated humerus is shown with two fractures, a first of which 18 occurs at the neck area. A second or distal fracture 20 occurs a distance downward from the head of the humerus. These fractures are across the major axis of the bone.

The apparatus of the present invention comprises an elongated intramedullary rod or pin having a proximal end 24 and a distal pointed end 26. The rod includes an enlarged self-tapping external screw 28 formed on the proximal or head end of the rod 22, defining or functioning as a compression screw. The rod 22 is provided with two angled cross bores 32 and 34 disposed in vertically spaced relation at an acute angle to the longitudinal axis of the rod 22. The bores 32 and 34 are also at an angle to one another about the longitudinal axis of the rod 22 as illustrated in FIG. 2. This angle is preferably about forty-five degrees the bore 32 as can be seen in FIG. 1 enters the rod 22 above the position where bore 32 enters the rod. The bore 32 extends upward to the left and the bore 34 extends upward to the right, below the bore 32.

The rod is preferably provided or made available in several sizes such as 7, 8, 9 and 10 mm. The compression screw 28 is formed in sizes 11, 12, 13 and 14, respectively. The rod is preferably available in length from 185 mm to 230 mm with intermediate lengths of about 210 mm. The cross bores may be about 4 mm for the smaller diameter rods up to about 6 mm for the larger diameter rods.

As shown in FIGS. 1 and 2, these cross bores are designed to receive a pair of interlocking screws 36 and 38 (shown in hidden lines) that extend at an angle to the longitudinal axis of the humerus between the two segments of the humerus. They extend across the fracture 18 and tie the two fragments of the bone together. These interlocking screws also extend at an angle of about forty-five degrees to one another when viewed along the axis of the humerus as in FIG. 2. They provide an "X" or cross configuration when viewed in the axial direction and may also cross in the transverse view. The compression at the head of the rod together with the cross interlocking provides a stable structure. The cross interlocking resists varus deforming forces as well as other forces and provides rotational stability.

The rod 22 is also preferably provided with at least one cross bore 40 near the proximal end thereof. In some instances, a second cross bore 44 may be provided distal of the proximal end thereof, particularly if additional fractures are present. The bore 40 extends at right angles to the longitudinal axis of the rod 22. It is designed to receive an interlocking screw 42. An optional bore 44 may also be provided near the distal end of the rod 22 for receiving an interlocking screw 46 in multiple fracture situations as illustrated. It is thus seen that the structure and apparatus is capable of tieing the sections of the fractured humerus together with the application of compressive longitudinal forces thereto. It also provides resistance to as well as preventing rotational misalignment.

Figure 6:
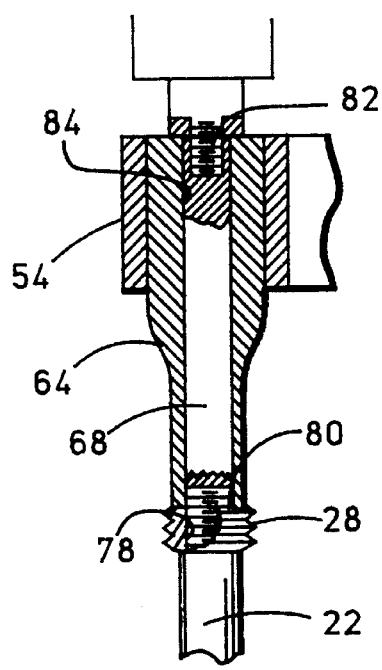
FIG. 6 is a detailed view, partially in section, illustrating an exemplary driving connection to the pin.
Figure 3:
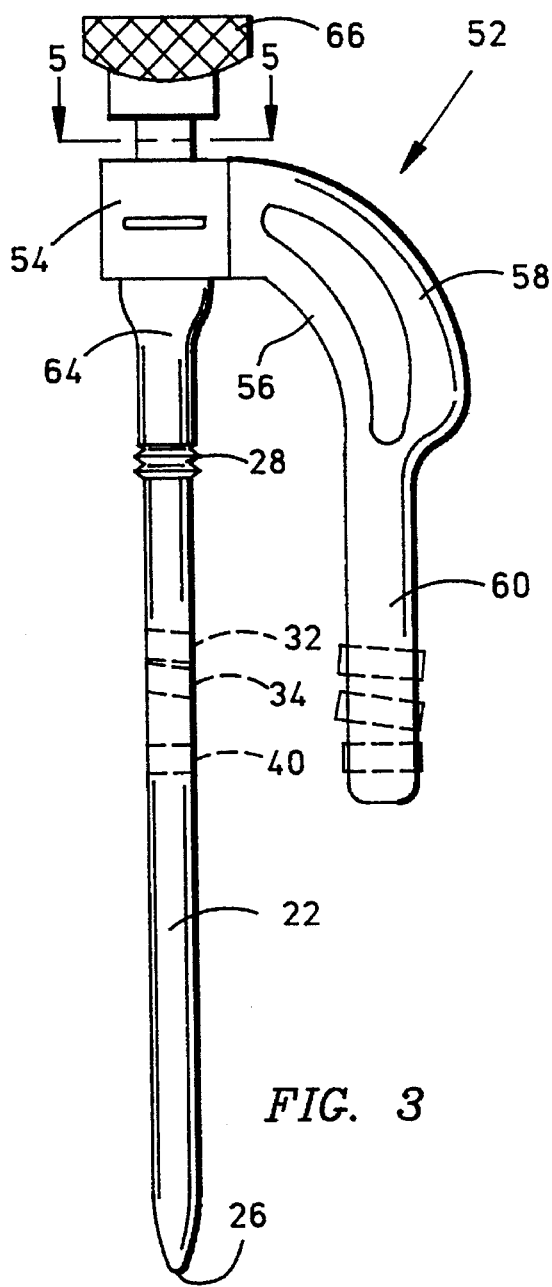
FIG. 3 is a front elevation view of a guide assembly shown attached to the pin of FIG. 1.
Figure 4:
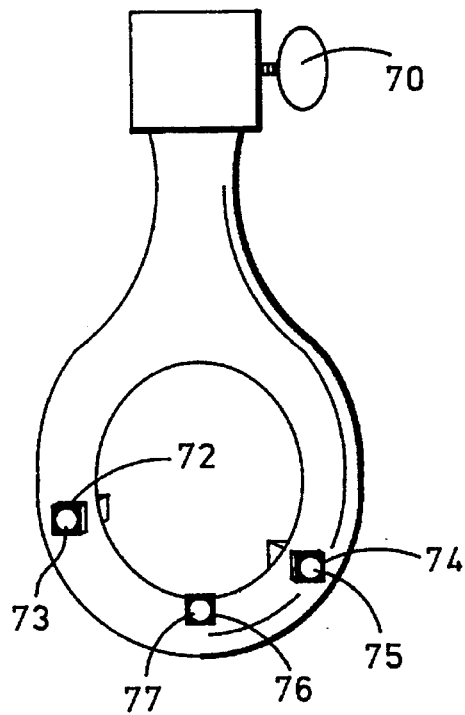
FIG. 4 is a side elevation view of the guide frame of the guide assembly of FIG. 3.

Referring to FIGS. 3–5, a guide fixture or device is provided for guiding the rod or pin 22 in position, and guiding the formation of holes for alignment of the interlocking screws with the bores 32, 34 and 40 of the rod 22. The guide frame comprises a main body, designated generally by the numeral 52, having a head 54, a central body portion, a main connecting member 56, a hand grasping body portion 58, and a lower guide member portion 60. The head portion has a bore 62 through which is inserted a hollow shaft or sleeve 64. The sleeve 64 rotatably mounts a removable extension shaft 68, with hand knob 66 on or connected to the upper end thereof. The lower end of the extension shaft is adapted to cooperatively engage and couple to the screw 28 at the upper end of shaft 22 as shown in FIG. 6.

This structure enables rotation of the rod 22 during insertion to fix screw 28 in place. This structure also enables alignment of the rod 22, such that the bores 32, 34 and 40 align with drill and screw guide cannulas in the lower body portion 60 of the guide frame. A thumb screw 70 is provided in the head 54 for engaging and clamping the shaft 64 in place in the head.

Referring to FIG. 4, the lower body portion 60 of the guide assembly has a generally circular configuration, with an uppermost guide bore 72 for alignment with bore 32. This bore receives a first cannula or sleeve 73 for guiding a drill for drilling a hole through the shaft of the humerus aligned with the bore 32. The sleeve is removed and screw 32 may be inserted through the bore 32. A second guide bore 74 similarly receives a drill guide sleeve 75 for first drilling a hole through the shaft of the humerus aligned with bore 34. Thereafter, the sleeve is removed and a screw inserted.

A lower bore 76 is adapted to receive a sleeve 77 for guiding a drill for drilling a hole in alignment with bore 40 of the rod 22. The sleeve is then removed and a screw inserted to align with the bore 40.

Referring to FIG. 6, a detailed view of the screw 28 and shaft coupling at the proximal end of the rod 22 is illustrated. The screw member 28 is of a generally cylindrical configuration and formed integral with the end of the rod and is preferably self-tapping. The screw is provided with coupling means, such as a central threaded bore 78 which receives a threaded end 80 of shaft 68. Other forms of couplings, such as bayonet can also be used. This shaft and socket arrangement couples the shaft 68 to the upper end of rod 22 to enable hand rotation of the rod 22 for threading the screw 28 into the proximal end of the humerus. It also provides coupling and support of the guide frame 52 and helps retain it in position relative to rod 22.

The hand knob 66 is removable from the upper end of shaft 68 to enable the guide frame 52 to be placed on and removed from the shaft 68. The knob 66 may be attached to the upper end of shaft 68 by any suitable means, such as a threaded stud 82 and socket 84, as illustrated. Other forms of couplings, such as a bayonet type, may also be used. The sleeve 64 is positioned in the bore 62 by means of different size key ways engaged by keys 86 and 88 in bore 62. The rod 22 is then indexed or aligned with suitable indicia on sleeve 64 for aligning bores 72, 74 and 76 with bores 32, 34 and 40.

In operation, a fracture as illustrated is stabilized with apparatus of the invention in accordance with the following procedure:

Make about a three cm long longitudinal incision of the skin proximally from the acromio-clavicular joint. Trapezius insertion to acromion and clavicle is exposed. The trapezius fascia attachment to acromion is split longitudinally, and the muscle is spread with a KELLY clamp. Under the trapezium muscle, there is a small fatty layer. After spreading the fatty layer, supraspinatus muscle will be identified. The muscle will be spread with a Kelly clamp in a longitudinal fashion. The synovial membrane underneath will be opened. Small self-retaining retractors may be used. Then, insertion of the supraspinatus tendon and other rotator cuff tendons will be observed or palpated from inside of the joint. Make an entry hole with an awl immediately medial to the insertion of the supraspinatus. Once the awl makes a hole in the proximal fragment, this awl is replaced by intermedullary rod which is already assembled with the guide system. Entry hole can be made from outside the supraspinatus insertion to humerus extra articularly, but in most cases there is not enough bony substance for an adequate purchase of fixation.

Prior to passing the rod into the distal fragment, the arm is brought up to seventy to ninety degrees abduction to bring the arm into an anatomically reduced position. Varus, valgus, anterior, and posterior angulation can be easily reduced. Once the rod is inserted, the rod has to be slightly counter sunk. The proximal screw 28 built on the rod is of a self-tapping kind. The final short distance of the rod will be inserted by rotation. There may be a slide latch on the guide system so that when the latch hits the articular surface, there is good indication that the rod is in the most ideal position. Also, this latch will give pressure to the proximal fragment against the distal fragment so that the fracture is in a compressed position. The two proximal lag screws 36 and 38 are inserted at this time. There should be two cannulas, one cannula fitting in the other. The inner cannula is for the drill, the outer cannula is for the screws. Prior to drilling, soft tissue spreading and protection of vital structure is very important. After two proximal lag screws are placed in an "X" configuration and interlocking screws insertion is accomplished, the guide system will be dissembled from the rod.

The main rod insertion is approached through the space superior to the acromion clavicle. This approach is not entirely new, because the superior porter in shoulder arthroscopic surgery is made from the same approach. The supra scapular nerve and artery are about one and one-half inches away. The nerve and vascular supply of the trapezius is farther medial and superior. Therefore, there is no immediate danger, but careful surgical technique is important.

While I have illustrated and described my invention by means of specific embodiments, it is to be understood that numerous changes and modifications may be made therein without departing from the spirit and scope of the invention as defined in the appended claims.

I claim:

1. A compression interlocking system for stabilizing upper arm fractures, comprising:

elongated intramedullary rod means having a proximal end, a distal end and a longitudinal axis, said rod means adapted for extending within a bore generally parallel to a longitudinal axis of a humerus from a proximal end of the humerus to beyond a fracture of the humerus;

a pair of transverse bores in the rod means for positioning adjacent the fracture; and a pair of lag screws for extending across said fracture and through said transverse bores, said transverse bores having longitudinal axes positioned and oriented so that said pair of lag screws positioned therein cross one another when viewed along both the longitudinal axis and in elevation view of the rod means, said bores being spaced along said axis of said rod means so that said pair of lag screws may be installed therein simultaneously without interference.

2. A system according to claim 1 wherein said intramedullary rod means further comprises an intermediate transverse bore disposed intermediate said pair of transverse bores and said distal end for positioning beyond the fracture; and at least one intermediate interlocking lag screw for traversing said humerus and rod means beyond said fracture.

3. A system according to claim 2 wherein said intramedullary rod means includes an enlarged self-tapping screw on the proximal end thereof.

4. A system according to claim 1 wherein said intramedullary rod means further comprises a distal transverse bore proximate said distal end for positioning beyond the fracture; and at least one distal interlocking lag screw for traversing said humerus and rod means beyond said fracture.

5. A compression interlocking system for stabilizing upper arm fractures, comprising:

elongated intramedullary rod means having a proximal end, a distal end and a longitudinal axis, said rod means including self-tapping screw means having a greater diameter than said rod means on the proximal end thereof, said rod means adapted for extending within a bore generally parallel to a longitudinal axis of a humerus from a proximal end of the humerus to beyond a fracture of the humerus;

a pair of transverse bores in the rod means for positioning adjacent the fracture, said transverse bores having longitudinal axis that cross one another when viewed along the longitudinal axis of the rod means; and a pair of lag screws for extending across said fracture and through said transverse bores.

6. A system according to claim 5 wherein said pair of transverse bores are at an angle to the longitudinal axis of the rod means so that the proximal lag screws form a cross when viewed in an elevation view of said rod means when installed.

7. A system according to claim 6 further comprising a guide frame having first guide means for alignment with said rod means and second guide means for aligning a drill for forming bores for aligning said pair of lag screws with said pair of transverse bores.

8. A system according to claim 6 further comprising a shaft having a hand knob on one end and means on the other end for detachably coupling to the proximal end of said rod for manually rotating said rod.

9. A system for compression interlocking and stabilizing upper arm fractures, comprising:

elongated intramedullary rod means having a longitudinal axis, a proximal end and a distal end, said rod means adapted for extending along a bore generally parallel to a longitudinal axis of a humerus from a proximal end of the humerus to beyond a fracture;

an enlarged self-tapping screw means mounted on the proximal end of said rod means;

a pair of transverse bores in the rod means adjacent the proximal end for positioning adjacent the fracture, said pair of bores having axes disposed at an angle to one another across the longitudinal axis of the rod means so that the axes of said bores form a cross when viewed along the axis of said rod means;

a pair of lag screws for extending across said fracture and through said pair of transverse bores; and at least an intermediate transverse bore in the rod means beyond the fracture; and at least one interlocking lag screw for traversing said humerus and said rod means at said intermediate transverse bore beyond said fracture.

10. A system according to claim 9 wherein said pair of transverse bores are at an angle to one another so that the pair of lag screws form a cross in elevation view when installed.

11. A system according to claim 10 further comprising a guide frame having first guide means for alignment with said rod and second guide means for aligning said pair of proximal lag screws with said pair of proximal transverse bores.

12. A system according to claim 10 further comprising:

first guide means comprising a first guide bore in a first end of said guide frame and shaft mounted in the bore for alignment with and coupling with said rod;

second guide means comprising a pair of second guide bores in a second end of said guide frame; and a drill cannula for insertion in each of said second guide bores for guiding a drill.

13. A method for compression interlocking and stabilizing of upper arm fractures, comprising:

selecting elongated intramedullary rod means having a longitudinal axis, a proximal end and a distal end and adapted for extending along a bore generally parallel to a longitudinal axis of a humerus from a proximal end of the humerus to beyond a fracture thereof, the rod means having an enlarged self-tapping screw means on the proximal end thereof, selecting the rod means to further have a pair of transverse bores in the rod means for positioning proximate the fracture, said bores disposed at an angle to the longitudinal axis of the rod means so that the axes thereof form a cross in axial view, along the axis of the rod means;

inserting said rod along a bore generally parallel to the longitudinal axis of the humerus from the proximal end of the humerus to beyond the fracture; and selecting a pair of proximal lag screws and inserting said screws across said fracture and through said transverse bores.

14. A method according to claim 13 wherein:

said rod means is selected to have at least an intermediate transverse bore in the rod means beyond the fracture; and inserting at least one intermediate interlocking lag screw traverse of said humerus and rod beyond said fracture from the proximal end of said humerus.

15. A method according to claim 13 further comprising the steps of selecting a guide system having first guide means for alignment with said rod and second guide means for aligning said pair of proximal lag screws with said pair of proximal transverse bores.

16. A system according to claim 15 wherein:

said first guide means comprises a first guide bore in a first end of a guide frame and a shaft mounted in the bore for alignment with and coupling with said rod means;

said second guide means comprises a pair of second guide bores in a second end of said guide frame; and a drill cannula for insertion in each of said second guide bores for guiding a drill.

* * * * *